United States Patent [19]
Perrier et al.

[11] Patent Number: 5,123,918
[45] Date of Patent: Jun. 23, 1992

[54] PROSTHETIC HEART VALVE

[75] Inventors: Philippe Perrier, St Nom La Breteche; Didier Lapeyre, Pacy s/Eure, both of France

[73] Assignee: Dassault Aviation, France; by said Philippe Perrier

[21] Appl. No.: 479,849

[22] Filed: Feb. 14, 1990

[30] Foreign Application Priority Data

Feb. 15, 1989 [FR] France ................. 89 01945

[51] Int. Cl.⁵ ............................................ A61F 2/24
[52] U.S. Cl. .............................................. 623/2
[58] Field of Search ................................. 623/2

[56] References Cited

U.S. PATENT DOCUMENTS

| | | | |
|---|---|---|---|
| 4,057,857 | 11/1977 | Fettel | 623/2 |
| 4,078,268 | 3/1978 | Possis | 623/3 |
| 4,488,318 | 12/1984 | Kaster | 623/2 |
| 4,820,299 | 4/1989 | Perrier et al. | 623/2 |
| 4,863,459 | 9/1989 | Olin | 623/2 |

FOREIGN PATENT DOCUMENTS

| | | |
|---|---|---|
| 133608 | 2/1985 | European Pat. Off. . |
| 207594 | 1/1987 | European Pat. Off. . |
| 289404 | 11/1988 | European Pat. Off. . |
| 2587614 | 3/1987 | France . |

*Primary Examiner*—Randy C. Shay
*Attorney, Agent, or Firm*—Bell, Seltzer, Park & Gibson

[57] ABSTRACT

A prosthetic heart valve comprising a base and at least two flaps. The valve includes means for guiding the flaps and for retaining them, said means being constituted, for each flap, by: two arcs for guiding the trailing edge of the flap; and at least one arc for guiding the leading edge of the flap. The invention is applicable to the manufacture of prosthetic heart valves.

14 Claims, 8 Drawing Sheets

PROSTHETIC HEART VALVE

The present invention relates to a mechanical prosthetic heart valve intended to be implanted in man to replace a natural heart valve which has been damaged by an infectious or a degenerative pathological process.

BACKGROUND OF THE INVENTION

Nowadays, there are known selection criteria which must be satisfied by a prosthetic heart valve. These criteria have been established by the Food and Drug Administration (FDA) which is the organization governing this field in the United States of America.

There are seven such criteria:

1) The first criterion is defined by the blood compatibility of the materials used. These materials must be compatible with the organism and they must behave inertly with respect to natural coagulation processes, i.e. they must not induce thrombosis phenomena on contact. A local thrombosis can give rise to embolism and can even hinder valve operation. Several materials behave satisfactorily from this point of view: specific metal alloys such as chromium, nickel-tungsten and titanium, and above all pyrolytic carbon, which is the material which is used most frequently nowadays in the valve prostheses that are commercially available 2) The second criterion is defined by the quality of the wake induced in the blood flow by the prosthesis. Zones of turbulence, eddies, and stagnant zones all give rise to the same phenomena of thromboses and embolisms, to such an extent that it has been said that the disturbances generated in the blood flow are more likely to generate thrombosis than the material used. That is why biological valves ("bioprotheses") which reproduce the form of the natural flow have a great advantage over mechanical prostheses. Such valves do not require anti-coagulant medication to be taken. These two thrombosis-generating factors (Material and Wake) are still imperfectly mastered on mechanical valve prosthesis, which means that patients must be put on anti-coagulants for life, thereby constituting a major drawback compared with bioprotheses.

Unforunately, that does not mean that biological valves constitute an ideal solution, since clinical experience shows that, unlike mechanical valves, their lifetime is too short. Because of their progressive deterioration, the surgeon often has to replace them at the cost of further major surgery. It has not been possible, in the past, to reproduce the flow characteristics of a natural valve when using a mechanical prosthesis. That is the object of the present invention.

3) The third criterion for mechanical valves is durability: in accelerated fatigue testing these valves must demonstrate that they have a lifetime equivalent to 560 million cycles, i.e. the equivalent of about 15 years under physiological working conditions (at a mean frequency of 70 heart beats per minute). This mechanical lifetime is related to the geometrical design of the valve, to the guide and abutment means adopted for the, or each, valve member or "flap" in the valve, and to the mechanical characteristics of the material used.

4) The fourth criterion is directly related to the second (Wake) and concerns the head loss which a mechanical prosthesis gives rise to on systolic ejection or on diastolic filling of the ventricle. A portion of such head loss is inevitable since it is inherent to the reduction in the effective orifice area (EOA), with the reduction in effective orifice area being related to the reduction in diameter caused firstly by the textile ring which is essential for surgical installation of the valve, and secondly by the thickness of the metal ring which supports the flap(s) and the hinge means enabling the flaps to move between an open position and a closed position. A second portion of the head loss is due to the geometrical disposition of the flap(s) and is mainly due to flap orientation relative to the flow of blood.

With a small anatomic orifice, in particular in a child, this factor is most important. Pressure gradients of more than 40 mm of Hg between the left ventricle and the aorta are thus commonly observed with 19 mm and 21 mm sizes, and this makes additional work for the heart muscle. This pressure gradient may reach higher values when the pumping rate of the heart increases. The surgeon is therefore happier using mechanical valves which, for given size, cause less stenosis.

5) The fifth criterion used concerns the closure time of the valve members when the ventricle contracts or relaxes. It is related to the geometrical definition of the valve and of its flap(s), and it determines the regurgitation fraction which at present, in the best of cases, is at least 5% of the volume of blood set into motion during each cycle. When a patient has two valves on the same ventricle, leakage is at least about 10%, and this puts non-negligible stress on the heart muscle.

6) The sixth criterion is static leakage, i.e. the mechanical sealing of the prosthetic valve when closed. For the same reasons, this criterion also has an influence on the hydraulic efficiency of the valve.

7) The seventh criterion may be considered as being the sum of the other six criteria: it concerns proper operation of the valve in man, as observed over a period of several years with the minimum possible number of thrombo-embolic incidents. A few mechanical valves give quite acceptable results. However, both moribity and mortality remain significant since the number of embolic incidents lies around 2% per annum and per patient, and mortality in many cases is of cardiac origin, and thus directly or indirectly linked to the valve prosthesis.

On this topic, it should be observed that these pathological phenomena are more common with patients having such a valve in the mitral position since the flow of blood through the valve in this configuration takes place at low pressure and for a longer period of time, thereby being more subject to thrombosis in the auricles, particularly since the prosthesis causes more stenosis, more regurgitation, and more turbulence, and is less well sealed.

In the mitral configuration, neither mechanical nor biological valve prostheses give full satisfaction. That is why it is important to improve existing products.

It may be recalled that the first prosthetic valves proposed in the early days of heart surgery, at the beginning of the 60s, were valves that attempted to reproduce the shape of natural heart valves. Because of their complexity and because of the technological possibilities available at that time, these prostheses were not reliable and they had to be abandoned. It was revolutionary when Star and Edwards proposed solving this problem by going right away from the natural model when they invented the valve constituted by a ball retained in a rigid cage. The function of the valve was thus reproduced reliably, albeit crudely. There are some surgeons who are still using this type of valve.

Manifestly the presence of a ball in the flow of blood gives rise to large head loss and to considerable disturbance in the flow. Observations made on man have confirmed this drawback. Later, Bjork proposed replacing the ball by a circular disk pivoting on a hinge device. Head loss was thus reduced. However, for mechanical reasons, it is not possible for the pivoting disk to tilt fully through 90°. The open angle is about 60° to 75°. There is thus a small orifice and a large orifice. It is easy to imagine that such an asymmetrical device has undesirable effects on the wake: there is a large zone of turbulence downstream from the valve over the small orifice, and this zone is responsible for thrombo-embolic phenomena, and, sometimes, for valve malfunction. These anomalies are clearly revealed nowadays by modern flow display techniques (Doppler-anemometry).

From the end of the 70s, a third generation of valve has provided a significant improvement on this point by using two half-disks pivoting on micro-hinges close to the diameter, instead of using a single tilting disk. The opening angle of both valve members comes close to perpendicular. The wake generated thereby is more symmetrical. Head losses are substantially reduced. Valves of this type are now the ones most frequently used in surgery on humans.

In summary, a single disk is better than a ball, and two half-disks (a genuinely "butterfly-like" valve) are better than a single disk. However, in valves of this type, the hinge axes of the valve members are centrally located in the zone of high speed flow, and since the opening angle is never 90° (since that would give rise to too high a regurgitation fraction), thrombosis-generating zones of turbulence remain with an imperfect wake.

U.S. Pat. No. 4,276,658 (corresponding to French patent FR-2-407 709) describes a heart valve prosthesis of the type comprising a body provided with a central blood flow passage, means for controlling this flow of blood, which means (flaps) pivot under the action of the blood flow between a closed position and an open position, and hinge means for the flow-controlling means.

The valve described in these patents includes hinge means comprising: cavities formed in the annular body of the valve presenting a bearing surface in the form of a surface of revolution, and flaps provided with projections intended to penetrate into the above-mentioned cavities with their ends sweeping the surfaces of revolution, each end being in contact with one of the bearing surfaces.

More precisely, the cavities are formed in the internal flat faces of two parallel and diametrically opposite lugs, projecting axially upstream from the periphery of the annular body of the prosthetic valve.

Although the valve of the above-mentioned patents is acceptable given the selection criteria mentioned above, it should nevertheless be observed that it does not reach optimum values of resistance to thrombosis because it has zones in which blood is at least partially stagnant, said zones being constituted by the cavities in which the projections of the flaps rotate. In addition, given that these flaps have only one degree of freedom, defined by rotation about an axis passing through two opposite cavities provided in the above-mentioned lugs, it is inevitable that the sweeping of the cavities is prejudicial to red corpuscles which are crushed therein. Further, the dynamic characteristics of the flow of blood through the valve are degraded by the central disposition of the flaps when in the open position, extending through the high-speed zone.

The Applicants have already proposed a prosthetic heart valve having excellent performance, particularly with respect to thrombosis resistance and to hemodynamics (which therefore satisfies the main two selection criteria for a prosthetic valve as underlined above), while also being highly satisfactory from the point of view of the other parameters defining the above-mentioned selection criteria. This prior valve constitutes the subject matter of French patent FR-2 587 614 and the corresponding U.S. patent application Ser. No. 06/910 621. In particular, it can easily be seen that in the valve of these two patents, account is taken of the influence on turbulence of the disposition of the closure flaps when in the open position, and also of the influence on closure time (i.e. how quickly the flaps close), when the direction of blood flow reverses. This valve also takes account of the anatomic configuration of natural heart valves, which are larger in section on the downstream side, corresponding:

in the mitral position, to the inlet into the ventricle; and in the aortic position, to the three sinuses.

More precisely, this prior valve takes account of the fact that the blood flow deviates (diverges) towards the wall of the valve in forward flow and that it converges towards the center of the valve in reverse flow.

In addition, the disposition of the flaps in the vicinity of the walls of the valve and the fact that the downstream ends of the flaps close towards the center of the valve clearly present several advantages:

the central portion of the valve where the flow is strongest is completely disengaged;

the flaps can be placed in a position where they lie parallel to the valve axis, thereby taking advantage of the convergent deviation of anatomic origin in reverse blood flow, as mentioned above, for initiating the closure movement; and since the flaps sweep through substantially the same zones when in motion as are swept through by the replaced natural valve, they run no risk of encountering obstacles to operation; in particular, a flap whose trailing edge opens from the periphery towards the center can run the risk of a possible fold in the tissue in the vicinity of the base preventing the flap opening at all, whereas in our prior valve, such a fold can at worse slightly limit full opening.

Naturally, when replacing an aortic valve, it would be preferable to place a single prosthetic valve with three flaps facing the three sinuses of the natural aortic valve replaced in this way. By placing the hinge axes of the flaps as close as possible to the wall and to the bottom edge of the flaps when in the open position, the flaps can be closed rapidly. Further, the valve includes appropriate means for minimizing wear of the means for guiding the flaps in rotation and for retaining them, thereby improving length of life and reliability of a prosthetic heart valve. These means for minimizing wear in the means for guiding the rotation of the flaps and for retaining them are the following:

maximum possible distance between the abutment point which limit flap motion during opening or closing so as to obtain the motion required for limiting the motion using the smallest possible forces;

increasing the areas of the flaps that come into contact with the base of the valve in the extreme positions so as to obtain the required forces using pressures which are as low as possible (this situation also contributes to reducing operating noise); and eliminating fixed spots of rubbing between the flaps and the base of the prosthetic valve during motion.

It is also easy to see that the structure of this prosthetic valve is such that all of its portions are accessible to the flow of blood during the course of an operating cycle, thereby avoiding the formation of zones of stagnant blood which encourage the formation of clots. To this end, the valve takes special care at the hinges of the flaps, whereas the problem of zones of stagnation is very poorly solved in most currently existing prosthetic valves because of the configurations adapted for their flat hinge means.

Although the valve constituting the subject matter of French patent FR-2 587 614 and U.S. patent application Ser. No. 06/910 621, as outlined above satisfies the above-mentioned selection criteria very well, in addition to the various other dispositions already mentioned, the present invention seeks to provide a prosthetic heart valve which, while satisfying the dispositions of the earlier valve, also includes means for guiding the rotation of the flaps and for retaining them which, while avoiding the formation of zones of stagnation in the blood flow, additionally have a configuration which lends itself to coating the body of the valve (including its means for guiding the flaps in rotation and for retaining them) with pyrolytic carbon, which is a material that is thrombosis resistant and which withstands wear.

SUMMARY OF THE INVENTION

The present invention provides a prosthetic heart valve comprising a base and at least two flaps, each flap comprising:

a leading edge which is in contact with the inside wall of the base in the closed position, and is situated at the upstream end of the flow in the open position;

a trailing edge which is in contact with the trailing edge(s) of the other flap(s) when in the closed position, and which is situated at the downstream end of the flow when in the open position;

two side edges constituting transition profiles between the leading edge and the trailing edge of each flap, each side edge delimiting, laterally and outwards, a transition zone corresponding to a corner of the flap and comprising an upstream segment belonging to the leading edge, and a downstream segment belonging to the trailing edge, the line defined by the succession of the leading edge, the trailing edge, and the side edges of each flap constituting the outline of the flap and delimiting two opposite faces, namely:

an inside face which is substantially parallel to the flow axis, when in the open position, and faces towards the middle of the flow; and an outside face which faces towards the inside wall of the base in the open position, and having at least a portion situated in the vicinity of each side edge making contact with the inside wall of the base in the open position, thereby constituting one of the means for limiting the opening motion;

the base being substantially annular in shape and comprising:

a leading edge situated at the upstream end of the flow; and a trailing edge situated at the downstream end of the flow, together with an outside wall for receiving suture means enabling the valve to be fixed to heart tissue; and said inside wall which extends in a direction substantially parallel to the flow and which supports means for guiding each flap in rotation and for retaining it;

wherein said means for guiding the flaps and retaining them are constituted, for each flap, by:

two trailing edge guide arcs each situated in the vicinity of one of the corners of the flap, each of said arcs beginning on the inside wall of the base at a point close to the trailing edge of the base and the transition zone between the trailing edge of the flap and one of the side edges of said flap in the open position, each arc extending towards the middle of the valve via a first portion which is substantially circular in shape so as to remain in the vicinity of the trailing edge of the flap throughout the motion thereof, the upstream end of said circular portion of the arc extending along a second portion which returns to the inside wall of the base at a point close to the leading edge thereof and serving as an abutment for the flap in its closed position; and at least one guide arc for the leading edge of the flap, said arc beginning from a point of the inside wall of the base situated close to the leading edge of the flap in the closed position, and upstream therefrom, and being substantially circular in shape such that it remains in the vicinity of the leading edge of the flap during its motion, said arc for guiding the leading edge extending towards the middle of the flow at least as far as the inside face of the flap in its open position, the end of said arc constituting an abutment for the leading edge of the flap in the open position and co-operating with the downstream portion of the arcs for guiding the trailing edges and with the inside wall of the base in order to avoid the flap escaping from its retaining means, said end extending to a point making contact with the inside face of the flap in the closed position, thus constituting an abutment point for the flap in the closed position.

In a preferred embodiment of the prosthetic heart valve of the invention, the guide arcs for the trailing edges corresponding to adjacent corners of two adjacent flaps meet at the common end of their circular portions and have a common second portion which returns to the inside wall of the base and which simultaneously serves as an abutment for both flaps in the closed position.

In another preferred embodiment of the prosthetic heart valve of the invention, the arcs for guiding the trailing edges of each flap are constituted by the edges of depressions formed in a projection from the inside wall of the base.

In a preferred disposition of this embodiment of the prosthetic heart valve, each projection from the inside wall of the base receives two depressions corresponding to the guide arcs for the trailing edges of two adjacent flaps, each of these depressions being formed in one of the two faces of said projection.

In another advantageous disposition of the prosthetic heart valve of the invention, the guide arc for the leading edges of each flap are situated close to those points on the leading edges of the flaps which move the least during flap motion.

In yet another advantageous disposition of the prosthetic heart valve of the invention, the leading edge of the base has a lip around at least a portion of its circumference, said lip being directed towards the middle of the flow and coming into contact with the leading edges of the flaps in the closed position, thereby improving the sealing provided by the flaps in said closed position.

In accordance with the invention, the section of the base of the prosthetic heart valve is either substantially circular in which case there are three flaps, or else substantially elliptical, in which case there are two flaps, with their trailing edges meeting in the closed position along a line running close to the long axis of the ellipse.

In yet another advantageous disposition of the prosthetic heart valve of the invention, the valve includes at least one additional guide means for each flap, said additional guide means being constituted, for each flap, by at least one projection or deformation on the inside wall of the base, at a point close to the leading edge of the flap in the closed position, and downstream therefrom, said projection or deformation being disposed in such a manner that its end remains in the vicinity of the outside face of the flap during its motion and thus serves as an abutment for said flap as it pivots.

In addition to the above dispositions, the invention includes further dispositions which appear from the following description.

BRIEF DESCRIPTION OF THE DRAWINGS

Embodiments of the invention are described by way of example with reference to the accompanying drawings, in which:

FIGS. 1 to 6 relate to a first embodiment of a prosthetic heart valve in accordance with the invention; and more particularly:

FIGS. 3 and 4 show the annular base of FIGS. 1 and 2 fitted with three flaps shown in the open position, whereas;

FIGS. 7 to 21 relate to a second embodiment of the prosthetic heart valve of the invention, and more precisely:

DETAILED DESCRIPTION

It should naturally be understood that the drawings and the corresponding portions of the description illustrate particular embodiments of the invention, but that the invention is broader in scope and also covers other prosthetic heart valves falling within the scope of the claims.

Figure 1:
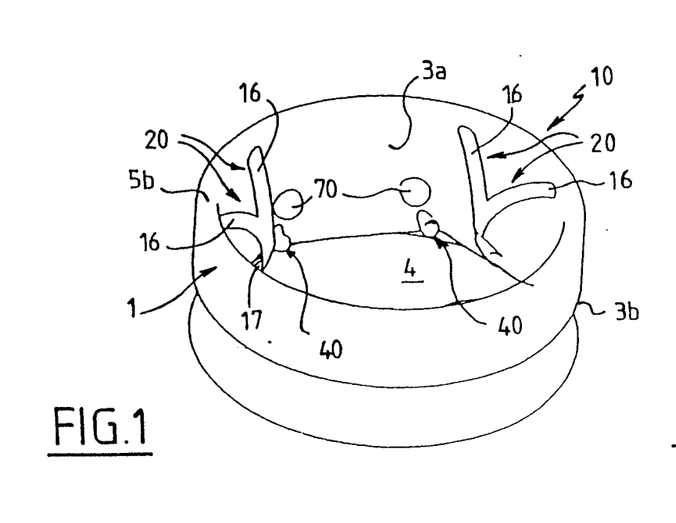
FIGS. 1 and 2 are perspective views of the annular flap-supporting base on its own as seen from above and from below, with the flaps omitted in order to show the disposition of the means for guiding and retaining the said flaps more clearly.
Figure 1A:
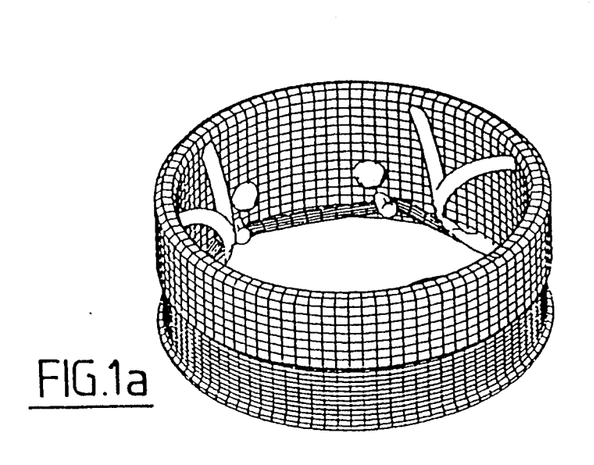
FIGS. 1a and 2a correspond exactly to FIGS. 1 and 2 except for the presence of shading lines serving to show up more clearly details relating to the means for guiding and retaining the flaps.
Figure 2:
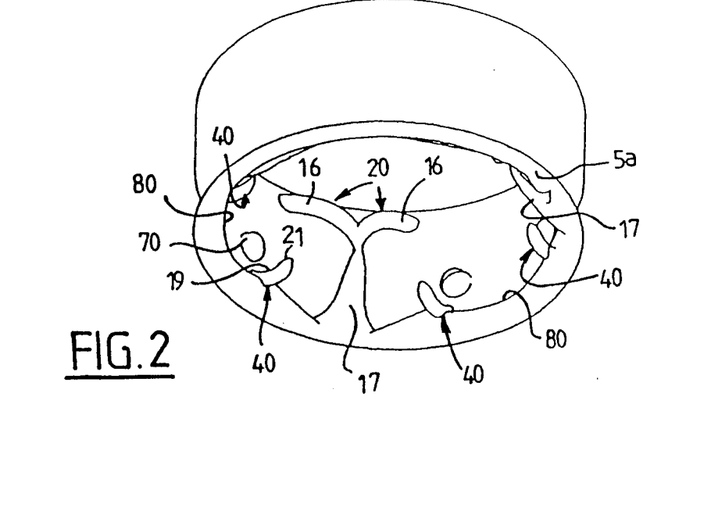
Figure 2A:
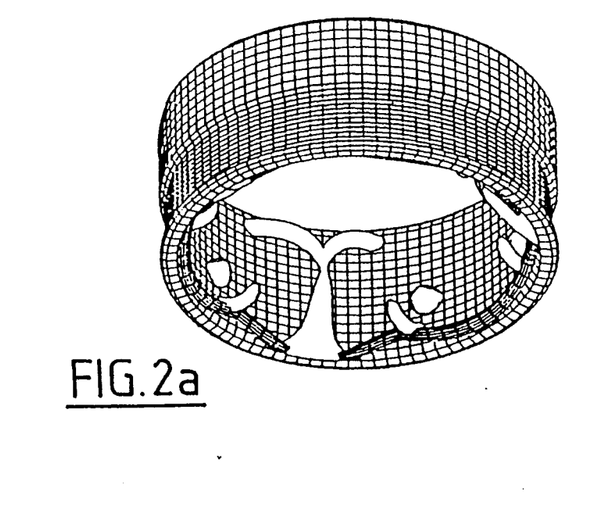
Figure 3:
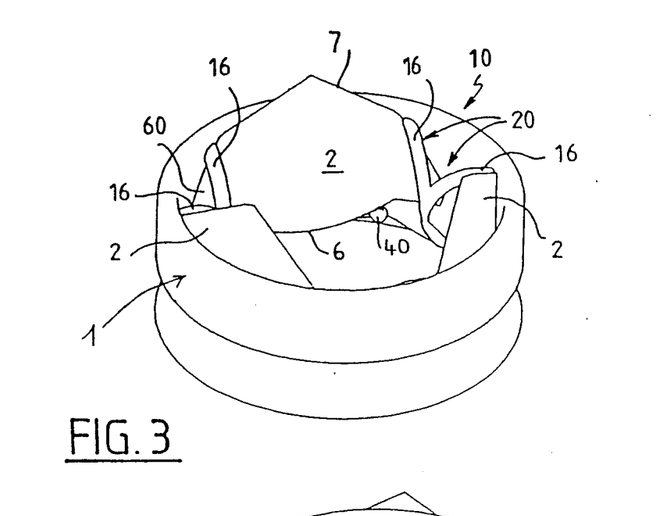
Figure 4:
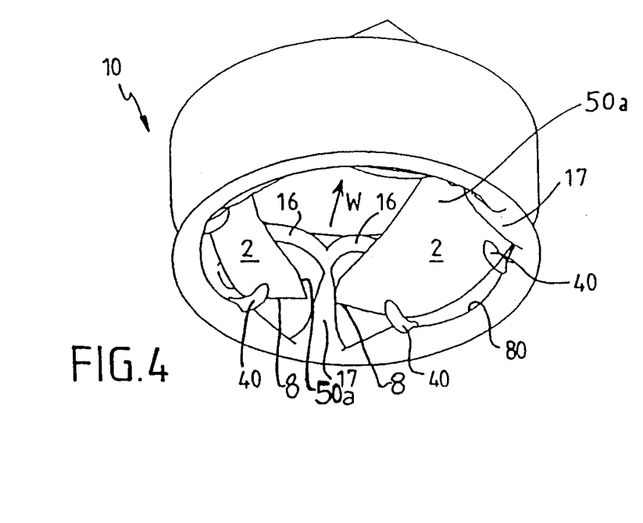
Figure 5:
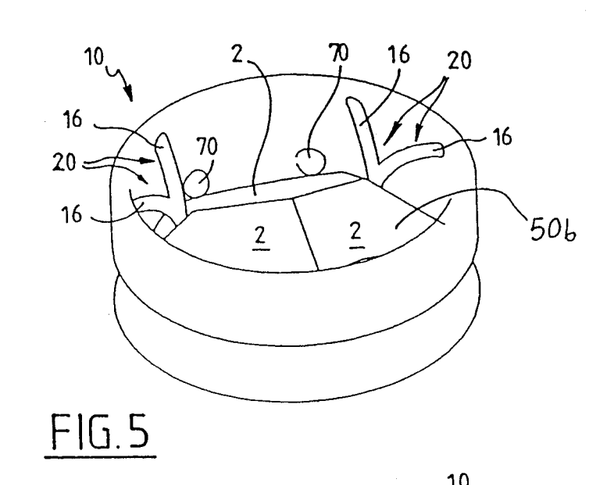
FIGS. 5 and 6 show the annular base of FIGS. 1 and 2 with the three flaps shown in the closed position.
Figure 6:
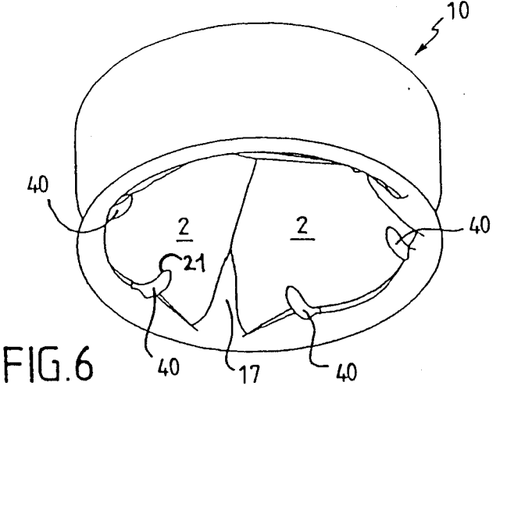

The heart valve 10 shown in FIGS. 1 to 6 comprises an annular base 1 for supporting three flaps 2. The base 1 has an outside wall 3b intended to receive suture means (not shown) enabling the valve to be fixed to heart tissue, and an inside wall 3a extending substantially parallel to the direction of flow and delimiting a central passage 4 for blood flow, together with a leading edge 5a situated at the upstream end of the flow and a trailing edge 5b situated at the downstream end. The three flaps 2 which are supported by the inside wall 3a of the base 1 are intended to control the flow of blood under the action of heart beats. The normal direction of blood flow is shown in FIG. 4 by an arrow W. The flaps are free to move between a closed position I as shown in FIGS. 5 and 6, and an open position II as shown in FIGS. 3 and 4. When the flaps are in the closed position I, they prevent the direction of blood flow being reversed towards the upstream end, whereas when they are in the open position II, they allow blood to flow downstream in the direction illustrated by above-mentioned arrow W in FIG. 4. Each flap comprises (cf. in particular FIGS. 3 and 4): a leading edge 6 which comes into contact with the inside wall 3 of the annular flap supporting base 1 when in the closed position (cf. FIGS. 5 and 6 in particular), and which is situated at the upstream end of the flow when in the open position; a trailing edge 7 which makes contact with the trailing edges of the other flaps of the prosthetic valve 10 when in the closed position (cf. FIGS. 5 and 6), and which is situated at the downstream end of the flow when in the open position; and two side (or transverse) edges 8 which are curved and convex and extend between the leading edge 6 and the trailing edge 7. The closed line defined by the leading edge 6, the trailing edge 7, and the two side edges 8 of each flap 2 constitutes the outline of the flap and delimits two opposite faces, namely an inside face 50a (FIG. 4) which, in the open position, lies substantially parallel to the flow axis and faces the central portion thereof, and an outside face 20b which, in the open position, faces towards the inside face of the base. Adjacent each side edge 8 is a transition zone which corresponds to a corner 60 of the flap and which comprises an upstream segment 9a belonging to the leading edge 6, and a downstream segment 9b belonging to the trailing edge 7. At least a portion of the outside surface of each corner 60 situated in the vicinity of the corresponding side edge makes contact with the inside wall of the base in the open position and thus constitutes one of the means for limiting the opening motion.

Means for guiding the rotation of each flap 2 and for retaining it between the open and closed positions I and II shown in FIGS. 5-6 and 3-4 respectively can be observed in FIGS. 1 to 6.

These means for guiding each flap in rotation and for retaining it are constituted by two arcs (or profiles) 20 for guiding and retaining the trailing edge 7 of the flap, together with two arcs (or profiles) 40 for guiding and retaining the leading edge 6 of the same flap.

Each of the arcs 20 for guiding the trailing edge 7 of a flap 2 is situated in the vicinity of one of its corners 60, beginning at a point on the inside wall 3a close to the trailing edge 5b of the base and the transition zone between the trailing edge 7 and one of the side edges 8 of the flap in the open position. Each arc 20 extends towards the middle of the valve via a first portion 16 which is substantially circular in shape so as to remain in the vicinity of the trailing edge 7 of the flap throughout the entire motion thereof.

At the upstream end of the first portion 16 of each arc 20 there extends a second portion 17 which returns to the inside wall 3a of the base at a point close to the leading edge 5a thereof, said second portion 17 serving as an abutment for the flap in the closed position.

In FIGS. 1 to 6, each pair of adjacent arcs 20 for guiding the trailing edges 7 of two adjacent flaps 2 includes two first portions 16 as mentioned above, and their upstream ends meet to extend upstream along a common second portion 17 belonging to both of the two adjacent arcs 20 and which thus serves simultaneously as an abutment for two adjacent flaps 2 in the closed position.

The two arcs 40 for guiding and retaining the leading edge 6 of a flap 2 begin at a point on the inside wall 3a of the base 1 situated close to the leading edge 6 of the flap when in the closed position, and situated upstream therefrom. Each arc 40 comprises a first portion 19 which is substantially circular in shape so as to remain in the vicinity of the leading edge 6 of the flap throughout its motion, and extending towards the middle of the flow at least as far as a point in line with the inside face 50a of the flap when in the open position. The radially inside end of each portion 19 thus constitutes an abutment for the leading edge of the corresponding flap when in the open position and co-operates with the downstream portion 16 of the arcs for guiding the trailing edge 7 and with the inside wall 3a of the base in order to prevent the flap from escaping from its retaining means.

The radially inside end of the portion 19 of each arc 40 extends along a second portion 21 to a point which is in contact with the inside face of the flap when in the closed position, thus constituting an abutment point for the flap when in said position.

FIGS. 1 to 6 (cf. in particular FIGS. 1 and 2) also show additional means for guiding each flap that may be provided on the inside walls 3a of the base. These means are constituted by pairs of projections (or deformations) 70 on said wall situated at points close to the leading edge 6 of the flap when in the closed position, and downstream therefrom. These projections 70 are disposed in such a manner that their ends remain close to the outside face 50b of the flap, while thus serving as an abutment for the flap during its motion.

The leading edge 5a of the base 1 has a lip 80 facing the middle of the flow and coming into contact with the leading edges 6 of the flaps 2 when in the closed position, thereby improving the sealing provided by the flaps when closed.

Figure 7:
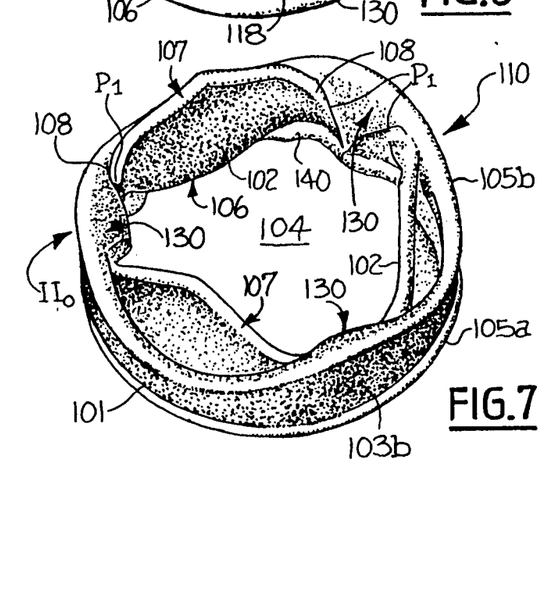
FIG. 7 is a perspective view of the prosthetic heart valve fitted with three flaps shown in the open position, as seen from a point situated above the valve.
Figure 8:
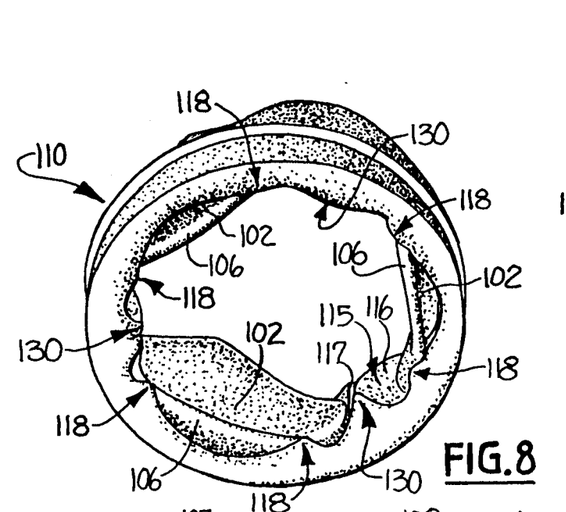
FIG. 8 is a perspective view of the valve shown in FIG. 7, as seen from a point of view below the valve.
Figure 9:
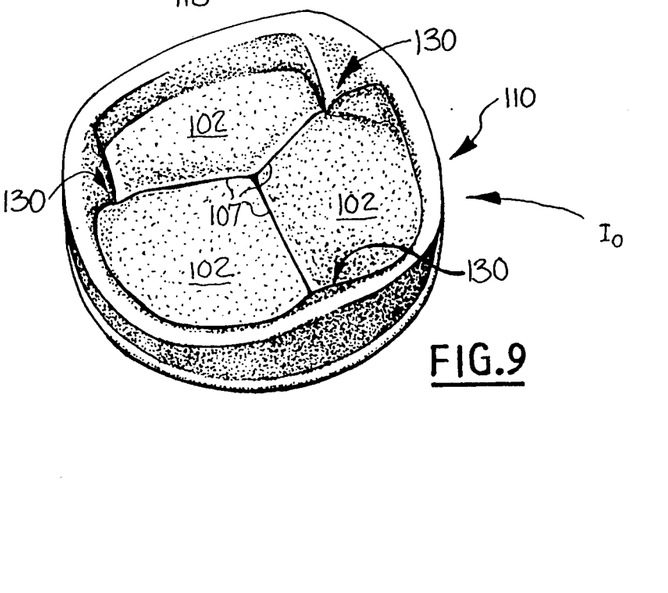
FIG. 9 is a view of the same valve as shown in FIGS. 7 and 8, with the flaps in the closed position and as seen from a point of view disposed above the valve.
Figure 10:
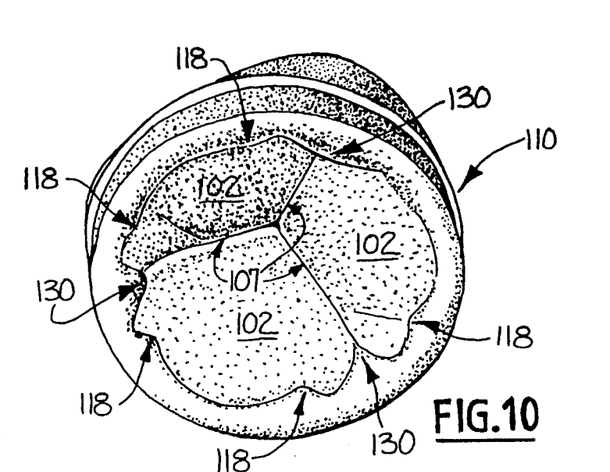
FIG. 10 is a view analogous to FIG. 9, and differs therefrom in that the point of view is from beneath the valve.
Figures 12, 14:
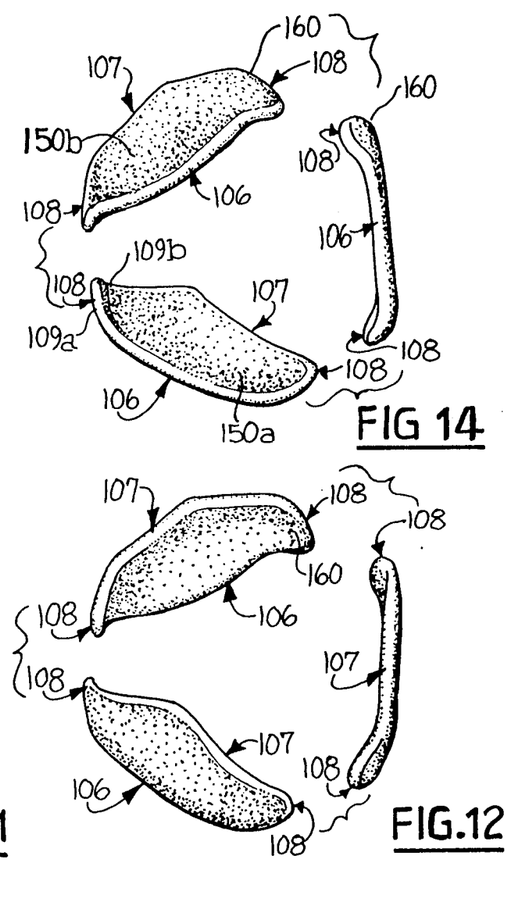
FIGS. 13 and 14 correspond to FIG. 8 with the component parts of the prosthetic valve being shown in exploded manner, i.e. with the base and the flaps being shown separated from one another.
Figure 13:
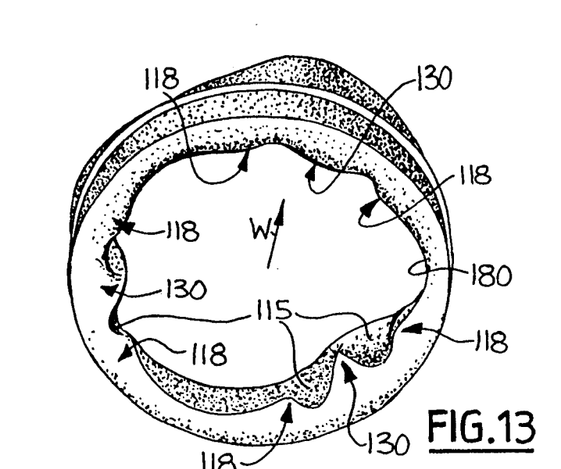
Figure 15:
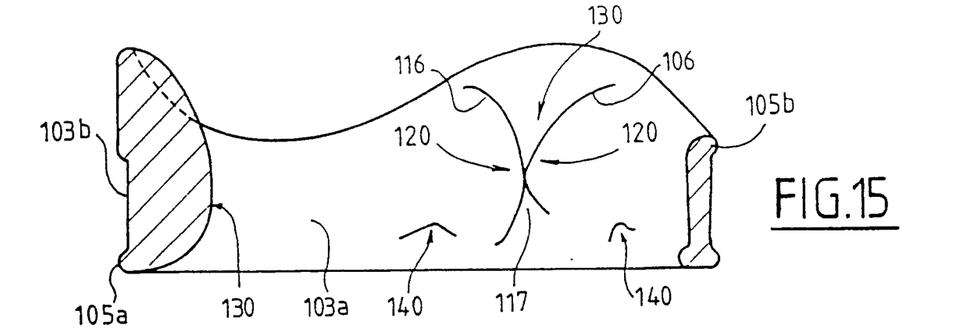
FIG. 15 is an axial section in elevation of the valve shown in FIG. 11.
Figure 16:
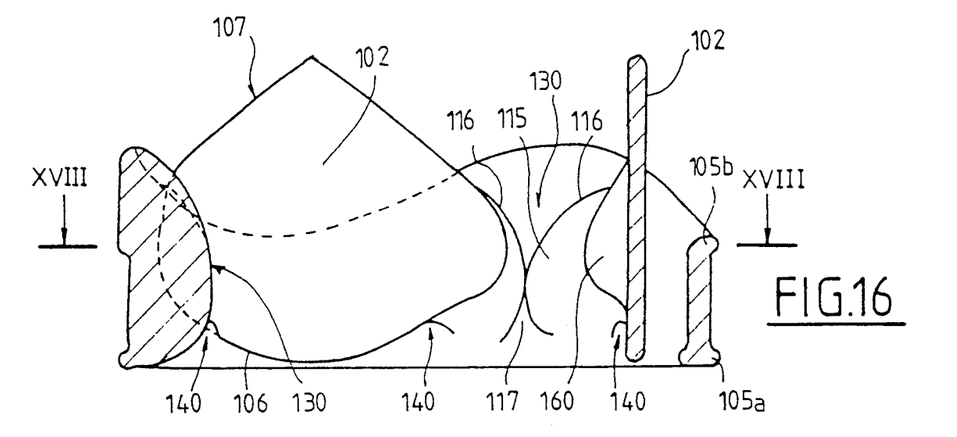
FIG. 16 is a section in elevation of the valve shown in FIG. 7.
Figure 17:
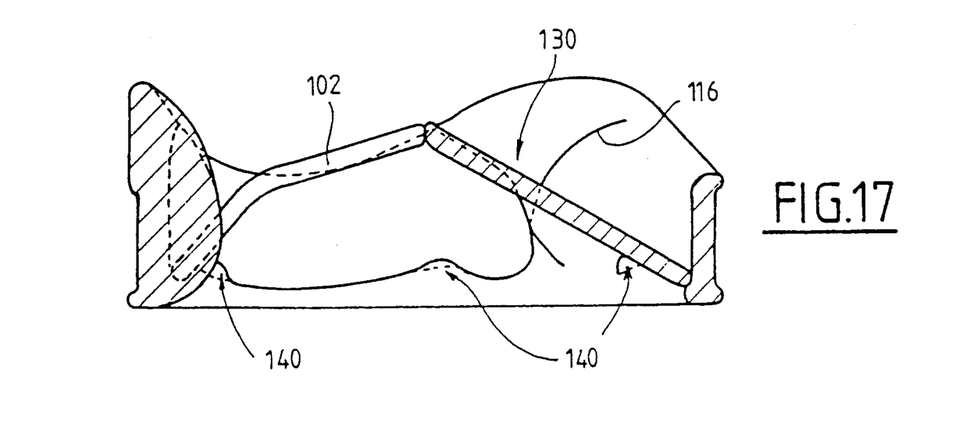
FIG. 17 is an axial section view of the valve shown in FIG. 9.

The heart valve 110 shown in FIGS. 7 to 21 comprises an annular base 101 for supporting three flaps 102. The base 101 has an outside wall 103b for receiving suture means (not shown) enabling the valve to be fixed to heart tissue, and an inside wall 103a which extends substantially parallel to the flow direction and which delimits a central passage 104 through which the blood is to flow, thus having a leading edge 105a at the upstream end of the flow and a trailing edge 105b at the downstream end of the flow. The three flaps 102 which are supported by the inside wall 103a of the base 101 are intended to control the flow of blood under the action of heart beats. The normal direction of blood flow is shown in FIG. 13 by an arrow W. The flaps move between a closed position $I_o$ as shown in FIGS. 9 and 10' and an open position $II_o$ as shown in FIGS. 7 and 8. When the flaps are in the closed position $I_o$ they prevent the blood flow direction reversing upstream, whereas when they are in the open position $II_o$, they allow blood to flow downstream in the direction shown by the above-mentioned arrow W in FIG. 13. Each flap comprises (cf. FIGS. 12 and 14 in particular): a leading edge 106 which in the closed position makes contact with the inside wall 103a of the annular flap support base 101 (cf. FIGS. 9 and 10 in particular), and which in the open position lies at the upstream end of the flow; a trailing edge 107 which, in the closed position, is in contact with the trailing edges of the other flaps of the prosthetic valve 101 (cf. FIGS. 9 and 10) whereas in the open position it is situated at the downstream end of the flow; and two lateral (or transverse) edges 108 which are curved and convex and which are defined by two transition profiles between the leading edge 106 and the trailing edge 107. The closed line defined by the succession of the leading edge 106, the trailing edge 107, and the two side edges 108 of each flap 102 constitutes the outline of the flap and delimits two opposite faces, namely an inside face 150a which lies substantially parallel to the flow axis in the open position and which faces the middle of the flow, and an outside face 105b which, in the open position, faces towards the inside wall of the base. Adjacent each side edge 108 is a transition zone which corresponds to a corner 160 of the flap and which comprises an upstream segment 109aa (FIG. 14) belonging to the leading edge 106, an a downstream segment 109b (FIG. 14) belonging to the trailing edge 107. At least a portion of the outside surface of each corner 160 situated in the vicinity of the corresponding side edge comes into contact with the inside wall 103a of the base in the open position and thus constitutes one of the means for limiting opening motion.

In FIGS. 7 to 21, means can be seen for guiding each flap 102 in rotation and for retaining it, as it moves between the closed and open positions $I_o$ and $II_o$ shown in FIGS. 9-10 and 7-8 respectively.

These means for guiding each flap in rotation and for retaining it are constituted by two arcs (or profiles) 120 for guiding and retaining the trailing edge 107 of the flap, together with two arcs (or profiles) 140 for guiding and retaining the leading edge 106 of the same flap.

Each arc 120 for guiding and retaining the trailing edge 107 of a flap 102 is formed in a radially inward projection 130 from the inside wall 103a of the base 101 supporting the flaps 102. In the figures, the number of projections 130 provided on the base 101 of the prosthetic valve 110 is equal to three so as to be able to guide the rotation of three flaps and to retain them, with each flap 102 extending between a pair of projections 130. Each projection 130 includes first and second identical depressions 115 which are oriented in such a manner that the depressions 115 corresponding to the corners 160 of a single flap 102 face each other. The edges of each of these depressions constitute the means for guiding and retaining a flap, and comprise in particular: a radially outer portion constituted by an extension of the inside wall 103a of the base 101, which portion comes into contact with the outside surface of the corner 160 of the corresponding flap when in the open position; and a radially inner portion corresponding to one of the arcs 120 for guiding and retaining the trailing edge 107 of a flap 102 and comprising:

a curved and convex downstream segment 116 for guiding the motion of a point P1 on the trailing edge 107 of the flap 102 (cr. FIG. 7 in particular), and situated on the downstream segment 109b of the corresponding side edge 108 of the flap, with guidance being provided as the flap moves from the open position $II_o$ to the closed position $I_o$, and vice versa; and a likewise curved and convex upstream retaining segment 117 constituting an abutment for the same above-mentioned point P1 when the flap 102 is in its closed position. Naturally, each depression 115 has a profile which fits the motion of a side edge 108 of a corresponding flap 102 as the flap moves between the open position $II_o$ and the closed position $I_o$, and vice versa.

It is thus clear that in the embodiment shown in FIGS. 7 to 21, the arcs 120 for guiding the trailing edges of the flaps are constituted by edges which delimit corresponding depressions formed in the projections on the inside wall of the base.

Each arc 140 for guiding and retaining the leading edge 106 of each flap 102 is constituted by the radially inner downstream portion of a projection 118 on the inside wall 103a of the support base 101.

This projection 118 comprises:

an inside segment 119 for guiding the motion of a point P2 on the leading edge 106 of the flap 102 (cf. FIG. 20), when the flap moves from the open position $II_o$ to the closed position $I_o$; and an outer, retaining segement 121, bearing against the same point P2 when the flap 102 passes from the closed position $I_o$ to the open position $II_o$. This curved profile outer segment 121 for guiding and retaining the leading edge 106 of the flap 102 extends slightly beyond the flap 102 when the flap is in its open position $II_o$.

Figure 11:
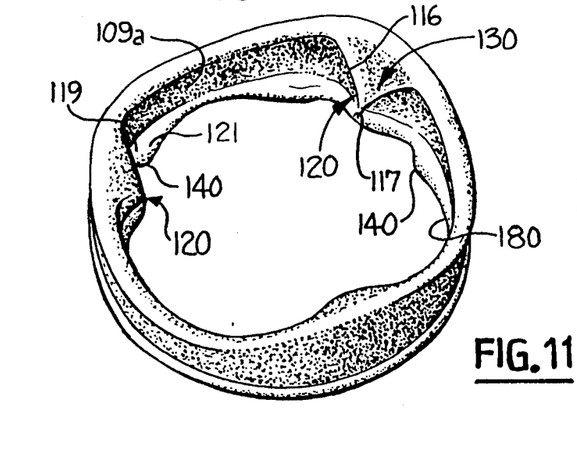
FIGS. 11 and 12 correspond to FIG. 7 with the component parts of the prosthetic valve being shown in exploded manner, i.e. the annular flap-supporting base and the flaps themselves are shown separated from one another.

A bearing lip 180 for the leading edge 106 of the flap 102 may also be provided in this case on the leading edge 105 of the base 101 of the prosthetic valve 110, as shown clearly in FIG. 11, in particular, where said lip 180 interconnects two consecutive projections 118.

It should be underlined that in both of the embodiments shown in FIGS. 1 to 6 and in FIGS. 7 to 21, the respective arcs 40 and 140 for guiding the leading edges of the various flaps are situated close to a point on the leading edge of each flap which describes the shortest displacement during flap motion.

The valve 110 of the present invention may also be provided with means for advancing closure, (i.e. means for anticipating flap closure on return of the blood flow in the reverse direction, thereby minimizing problems of regurgitation), said means being as described in the Applicants' French and American patents as mentioned above. These means are essentially constituted by magentic masses (FIG. 19) which are incorporated in each flap so that the corners of two contiguous flaps have magnetic polarities of opposite signs and are capable of co-operating with additional magnetic masses disposed in the base of the prosthetic valve between pairs of contiguous flaps, and occupying a space equal to the distance that exists between the adjacent corners of contiguous flaps in the open position. Each of these additional magnetic masses is disposed in the base in such a manner that its polarities correspond to the opposite-sign polarities of the magnetic masses provided in the corners of the flaps.

Naturally, the above-mentioned magnetic masses are designed so that the attraction between adjacent flap corners (for closing the valve) exactly counters the pressure and friction forces tending to open the flaps when the flow speed in the forward direction reaches a certain percentage of its maximum value. This means that by virtue of the closure advance means, closure will begin before the flow reverses.

The magnetic masses may be constituted in conventional manner for the person skilled in the art by small permanent magnets fixed on the corners of the flaps and on the base by any appropriate means, or by incorporating magnetic material in the manufacture of the prosthetic valve in a form which is finely dispersed in the corners of the flaps and in the base in appropriate positions, as shown in FIGS. 2, 3 and 3a of the above-mentioned French and American patents in the names of the Applicants.

With reference to FIGS. 15 to 21 (which are mostly section views, except for FIG. 19 which is a plan view), these figures serve to clarify details of the structure of a prosthetic valve of the invention as shown in perspective in FIGS. 7 to 14 as described above.

Naturally the prosthetic heart valves 10 of the present invention also satisfy all of the dispositions mentioned in the French and American patents in the name of the present Applicants, and recalled on several occasions in the body of the present description, including the indications therein concerning appropriate choices for materials suitable for being used in the construction of the valve, and in particular the preferred choice of pyrolytic carbon. It can easily be seen that the configuration of the means for guiding the flaps and retaining them in a prosthetic valve of the present invention lends itself particularly well to manufacture with a coating of pyrolytic carbon, not only at the base of the valve prosthesis, but also over the projections 118 and 130 in which the profiles are formed for guiding the rotation of the leading and trailing edges of each flap, and for retaining them.

It should also be observed that each of the depressions 115 formed in the projections 130 differs from one of the cavities in the prosthetic valve of above-mentioned patents FR-2 407 709 and U.S. Ser. No. 847,780, in that there exists no point on the corresponding corner of the flap which remains at a fixed location in the depression 115 during motion. This operating condition enables the depression to be swept fully during each cycle, thereby avoiding any danger of stagnation, and it is made possible by virtue of the co-operation between the guiding and retaining arcs 140 and the leading edges 106 of the flaps 102.

Figure 18:
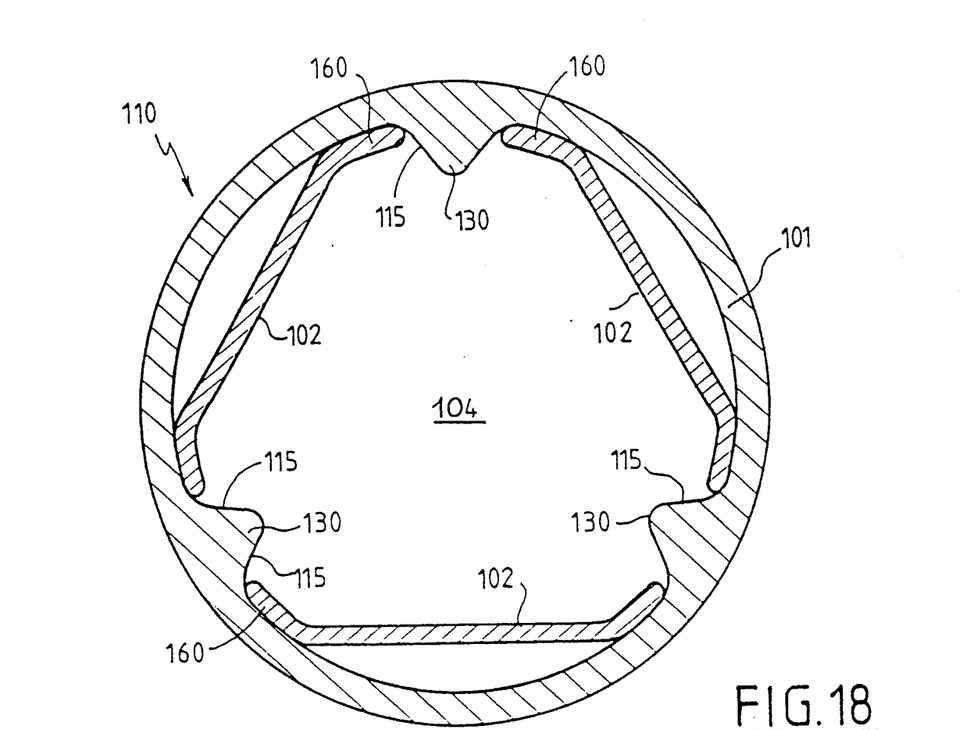
FIG. 18 is a section of the valve on plane XVIII of FIG. 16.
Figure 19:
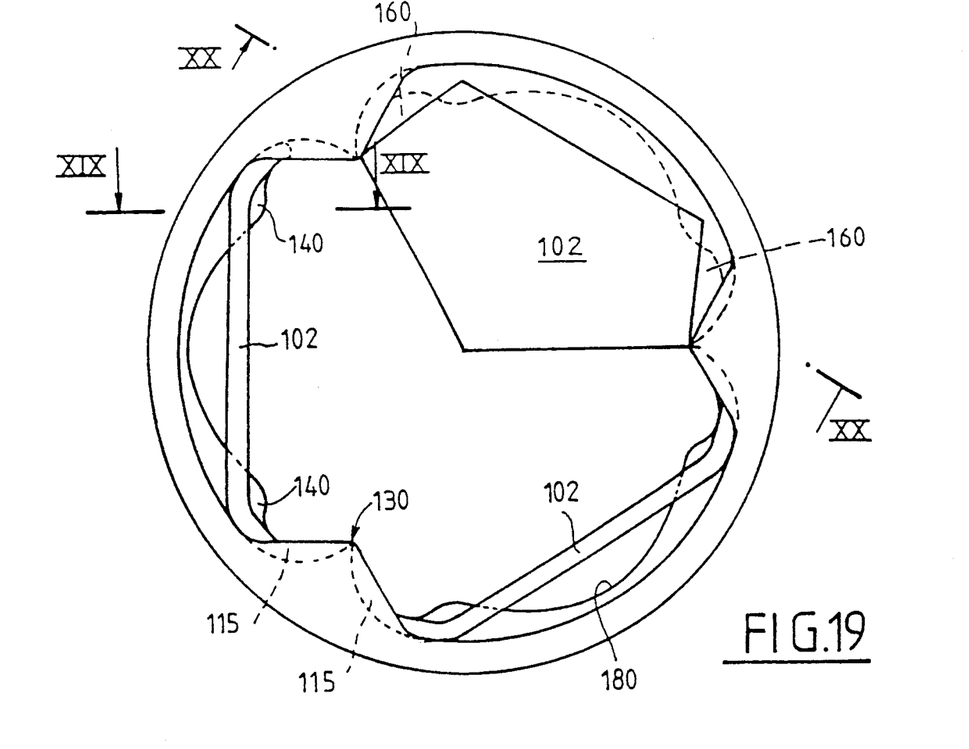
FIG. 19 is a plan view of the valve as shown in FIGS. 7 and 9, i.e. with two flaps in the open position and with one flap in the closed position.
Figure 20:
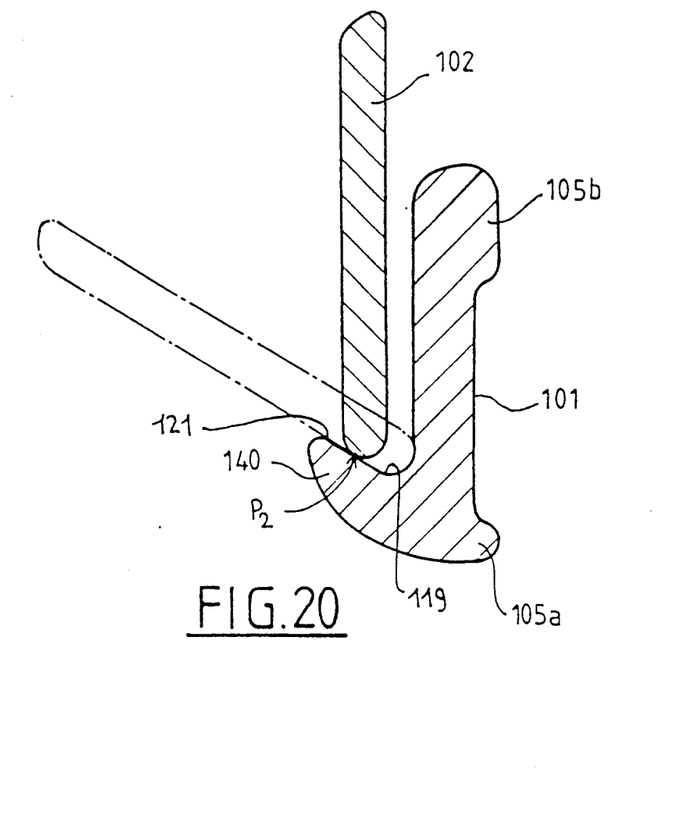
FIG. 20 is a section view on plane XIX of FIG. 19.
Figure 21:
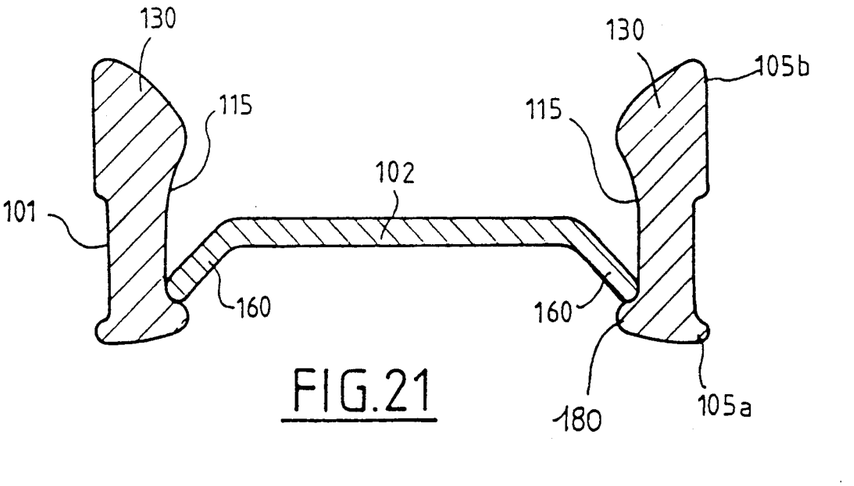
FIG. 21 is a section view on plane XX of FIG. 19, and corresponds to the flap being shown in the closed position.
Figure 22:
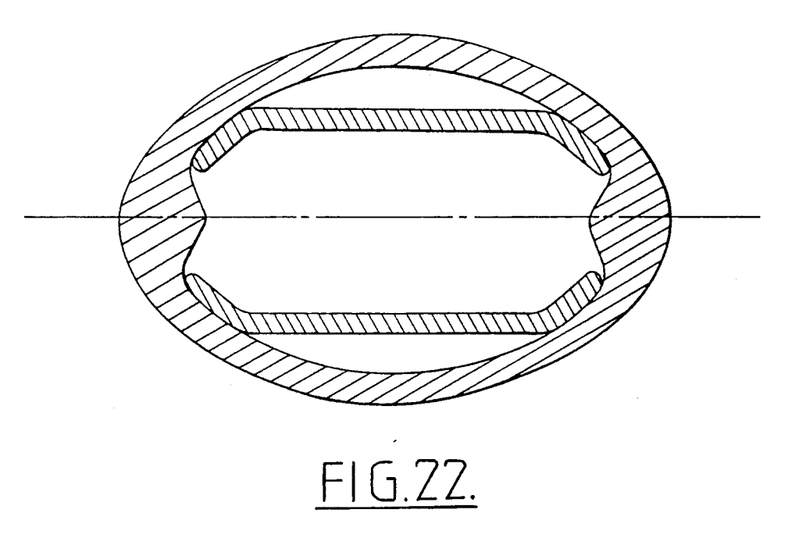
FIG. 22 is a section view similar to that of FIG. 18 illustrating an alternative embodiment with an elliptical base and two flaps.

FIG. 22 is a view similar to FIG. 18 of an alternative embodiment in which the base is substantially elliptical and there are two flaps.

We claim:

1. A prosthetic heart valve comprising a base having an inside wall and a plurality of flaps, each flap comprising:

a leading edge which is in contact with the inside wall of the base in the closed position, and is situated at the upstream end of the flow in the open position;

a trailing edge which is in contact with the trailing edges of the other flaps when in the closed position, and which is situated at the downstream end of the flow when in the open position;

two side edges between the leading edge and the trailing edge of each flap, each side edge defining an area corresponding to a corner of the flap and comprising an upstream segment belonging to the leading edge, and a downstream segment belonging to the trailing edge, the line defined by the succession of the leading edge, the trailing edge, and the side edges of each flap constituting the outline of the flap and delimiting two oppostie faces, namely:

an inside face which is substantially parallel to the flow axis, when in the open position, and faces radially inward; and an outside face which faces radially outward towards the inside wall of the base in the open position, and having at least a portion situated in the vicinity of each side edge making contact with the inside wall of the base in the open position, thereby constituting means for limiting the opening motion;

said base being substantially annular in shape and comprising:

a leading edge situated at the upstream end of the flow; and a trailing edge situated at the downstream end of the flow, and an outside wall for receiving suture means enabling the valve to be fixed to heart tissue; and said inside wall extending in a direction substantially parallel to the flow and having means for guiding each flap in rotation and for retaining it;

wherein said means for guiding each of the flaps and for retaining them comprise:

two trailing edge guide arcs each situated in the vicinity of one of the corners of each flap, each of said arcs beginning on the inside wall of the base at a point close to the trailing edge of the base and the zone between the trailing edge of the flap and one of the side edges of said flap in the open position, each arc extending radially inward towards the middle of the valve via a first portion which is substantially circular in shape so as to remain in the vicinity of the trailing edge of the flap throughout the motion thereof, the upstream end of said circular portion of the arc extending along a second portion which returns to the inside wall of the base at a point close to the leading edge thereof and serving as an abutment for the flap in its closed position; and at least one leading edge guide arc for the leading edge of the flap, said at least one leading edge guide arc beginning from a point of the inside wall of the base situated close to the leading edge of the flap in the closed position, and upstream therefrom, and being substantially circular in shape such that it remains in the vicinity of the leading edge of the flap during its motion, said arc for guiding the leading edge extending radially inward at least as far as the inside face of the flap in its open position, the end of said at least one leading edge guide arc constituting an abutment for the leading edge of the flap in the open position and co-operating with the downstream portion of the arcs for guiding the trailing edge and with the inside wall of the base in order to avoid the flap escaping from its retaining means, said end of said at least one leading edge guide arc extending to a point making contact with the inside face of the flap in the closed position, thus constituting an abutment point for the flap in the closed position.

2. A prosthetic heart valve according to claim 1, wherein the guide arcs for the trailing edges corresponding to adjacent corners of two adjacent flaps meet at the common end of their circular portions and have a common second portion which returns to the inside wall of the base and which simultaneously serves as an abutment for both flaps in the closed position.

3. A prosthetic heart valve according to claim 1, wherein the arcs for guiding the trailing edges of each flap are constituted by the edges of a projection from the inside wall of the base.

4. A prosthetic heart valve according to claim 3, wherein each projection from the inside wall of the base corresponds to the guide arcs for the trailing edges of two adjacent flaps.

5. A prosthetic heart valve according to claim 1, wherein the guide arc for the leading edges of each flap are situated close to those points on the leading edges of the flaps which move the least during flap motion.

6. A prosthetic heart valve according to claim 1, wherein the leading edge of the base has a lip around at least a portion of its circumference, said lip being directed radially inwardly and coming into contact with the leading edges of the flaps in the closed position, thereby improving the sealing provided by the flaps in said closed position.

7. A prosthetic heart valve according to claim 1, wherein the base is substantially circular in section, and wherein the flaps are three in number.

8. A prosthetic heart valve according to claim 1, including at least one additional guide means for each flap, said additional guide means being constituted, for each flap, by at least one projection or deformation on the inside wall of the base, at a point close to the leading edge of the flap in the closed position, and downstream therefrom, said at least one projection or deformation being disposed in such a manner that its end remains in the vicinity of the outside face of the flap during its motion and thus serves as an abutment for said flap as it pivots.

9. A prosthetic heart valve according to claim 1, wherein each of the flaps is provided with closure advance means, means for anticipating flap closure relative to the blood flow direction reversing.

10. A prosthetic heart valve according to claim 9, wherein said closure advance means are constituted by magnetic masses of opposite polarities provided in the corners of each flap with the magnetic polarities of two adjacent corners of two different flaps being opposite.

11. A prosthetic heart valve according to claim 10, wherein said magnetic masses provided in the corners of each flap cooperate with additional magnetic masses which are disposed in the base between two adjacent flaps and occupy a distance substantially equal to the distance between the adjacent corners of the two adjacent flaps in the open position, each additional magnetic mass being disposed in the base in such a manner that its magnetic polarities correspond to the opposite-sign polarities of the magnetic masses provided in the corners of the flaps.

12. A prosthetic heart valve according to claim 10, wherein said magnetic masses are constituted by small magnets.

13. A prosthetic heart valve according to claim 10, wherein said magnetic masses are constituted by magnetic material incorporated in each flap or in the base during manufacture thereof.

14. A prosthetic heart valve according to claim 1, wherein the base is substantially elliptical in section and wherein the flaps are two in number, their trailing edges meeting in the closed position along a line lying close to the long axis of said ellipse.

* * * * *